United States Patent
Yang et al.

(10) Patent No.: US 7,052,512 B2
(45) Date of Patent: May 30, 2006

(54) FLUORESCENT DYED LUBRICANT FOR MEDICAL DEVICES

(75) Inventors: Dachuan Yang, Plymouth, MN (US); Liguang Tang, Plymouth, MN (US); Dixie Lang, Minnetonka, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 94 days.

(21) Appl. No.: 09/908,070

(22) Filed: Jul. 18, 2001

(65) Prior Publication Data
US 2003/0018353 A1 Jan. 23, 2003

(51) Int. Cl.
*A61F 2/06* (2006.01)

(52) U.S. Cl. ...................... 623/1.46; 623/1.23

(58) Field of Classification Search ............... 623/1.34, 623/1.46; 606/76, 194; 604/265
See application file for complete search history.

(56) References Cited

U.S. PATENT DOCUMENTS

| | | | | |
|---|---|---|---|---|
| 5,266,359 A | * | 11/1993 | Spielvogel | 604/265 |
| 5,670,097 A | * | 9/1997 | Duan et al. | 264/1.24 |
| 5,807,605 A | | 9/1998 | Tingey et al. | 427/8 |
| 5,858,746 A | * | 1/1999 | Hubbell et al. | 435/177 |
| 6,254,634 B1 | * | 7/2001 | Anderson et al. | 623/1.42 |
| 6,447,501 B1 | * | 9/2002 | Solar et al. | 604/528 |

* cited by examiner

*Primary Examiner*—Eduardo C. Robert
*Assistant Examiner*—Jessica R Baxter
(74) *Attorney, Agent, or Firm*—Vidas, Arrett & Steinkraus

(57) ABSTRACT

A composition and method for detecting the presence, location and uniformity of a lubricious coating on a medical device. The method includes the steps of preparing a mixture of a biocompatible hydrophilic fluorescent dye and a hydrophobic lubricant, applying the mixture to the surface of a medical device to form a coating capable of exhibiting fluorescence, and subjecting the surface of the medical device to a source of energy capable of inducing a fluorescent emission. The coating composition may further comprise a surfactant. This method finds particular utility for catheters, especially stent delivery catheters.

15 Claims, 4 Drawing Sheets

FLUORESCENT DYED LUBRICANT FOR MEDICAL DEVICES

FIELD OF THE INVENTION

The present invention relates to composition and method for detecting the presence, location and uniformity of a lubricious coating on a medical device. The composition includes a lubricant and a fluorescent dye. The invention further includes a method of visualizing and observing the coating by irradiating the coating with an energy source capable of inducing fluorescence, and observing the fluorescence of the coating. In some embodiments, the invention can provide for nondestructive visualization and observation of a coating to determine presence, location and uniformity of the coating.

BACKGROUND OF THE INVENTION

Intraluminal medical devices such as catheter assemblies are often inserted into a patient at a location remote from the treatment site. For instance, these devices are often inserted into the femoral artery in the groin area, and are then maneuvered through the femoral artery and into position in the upper cardiovascular region. The materials routinely used in the manufacture of such devices are often not inherently lubricious. In order to facilitate insertion and navigation through the body vessels and to therefore make this type of procedure less traumatic for the patient, lubricious coatings can be applied to the surfaces of the devices to reduce the friction between the device surface, and whatever other surface with which it comes into contact.

Lubricants come in both hydrophilic and hydrophobic varieties. Hydrogels are one class of hydrophilic lubricants. Hydrophobic lubricants include oils such as olive oil and sesame oil, glycerine, and silicone based compounds.

One commonly used silicone lubricant is polydimethylsiloxane. This lubricant is a clear, water white liquid that is typically applied to the surface of a medical device as a solution, or it may be applied neat. The lubricant is applied in very small amounts. The clarity and amount of coating applied, along with the very small size of these medical devices makes visual inspection of the amount and location of the coating very difficult, however. Adding color to the coating in the form of a dye or pigment is typically not a desirable option when used on medical devices.

A couple of different methods have been utilized to determine the presence and adequacy of a lubricious coating but they are considered as being "destructive" methods. The first is to carefully weigh pre-identified catheters, run them through the coating process, and then weigh them again to determine coat weight. This allows a gross determination of the amount of coating (such as a silicone coating) on a catheter, but is considered to be a destructive method because the identified catheter cannot be used. Furthermore, this does not allow visualization as to where the coating is located on the device, or the quality or uniformity of the coverage.

A second method involves removing the coating from the surface of the catheter with a solvent, evaporating the solvent, and weighing the coating. This method is more cumbersome, and it also does not indicate the quality or uniformity of the coverage.

U.S. Pat. No. 5,807,605 describes a non-destructive method for visualization of a polydimethylsiloxane coating on a surface of a medical device which includes dissolving a fluorescent agent into the polydimethylsiloxane lubricant and applying the fluorescenated polydimethylsiloxane lubricant to the surface of the medical device.

SUMMARY OF THE INVENTION

In one embodiment, the present invention relates to a nondestructive method for the visualization of a hydrophobic lubricious coating on the surface of a medical device using a hydrophilic fluorescent dye. The dye is preferably biocompatible. The method includes the steps of preparing a mixture if a hydrophobic lubricant and a hydrophilic dye, coating the surface of a medical device with the mixture, irradiating the surface of the medical device with a source of energy capable of inducing fluorescence.

The method can also include the step of observing the fluorescent emission to determine the presence and location of the lubricious coating.

In another embodiment, the present invention relates to a medical device, having a hydrophobic lubricant with a biocompatible hydrophilic fluorescent dye disposed on its surface.

The medical device may be an intraluminal medical device such as a stent.

In another embodiment, the present invention relates to a method for determining the presence and location of a lubricious coating on the inner surface of a stent retaining sleeve including the steps of adding a fluorescent dye to a lubricant, applying the lubricant to the inner surface of the stent retaining sleeve, and exposing said inner surface of said stent retaining sleeve to a source of energy capable of inducing fluorescence.

The method may further include the step of observing the fluorescent emission to determine the presence and location of the lubricious coating.

The lubricious coating may include either hydrophilic or hydrophobic lubricants. Suitably, at least one lubricant is hydrophobic.

In another embodiment the present invention relates to a stent delivery system including a stent delivery catheter equipped with at least one, and preferably two, stent retaining sleeves. The stent retaining sleeves are further characterized as having an inner surface and an outer surface, and a hydrophobic lubricious coating with a fluorescent dye disposed on at least the inner surface.

In some specific embodiments of the present invention, the fluorescent dye is biocompatible and is hydrophilic. Some particularly useful biocompatible, hydrophilic dyes are 5-carboxyfluorescein or 6-carboxyfluorescein or a mixture thereof.

In another aspect, the present invention relates to a lubricious composition including a hydrophobic lubricant and a hydrophilic fluorescing agent. The composition may be prepared by mixing the lubricant and the fluorescing agent. The mixing may optionally be accomplished through the use of a surfactant, and may also be accomplished through the use of a cosolvent blend.

In an alternative embodiments, the lubricant itself is fluorescenated through the addition to the lubricants molecules of groups capable of emitting fluorescent radiation.

BRIEF DESCRIPTION OF THE DRAWINGS

A detailed description of the invention is hereinafter described with specific reference being made to the following figures.

DETAILED DESCRIPTIONS OF THE PREFERRED EMBODIMENTS

Figure 1:
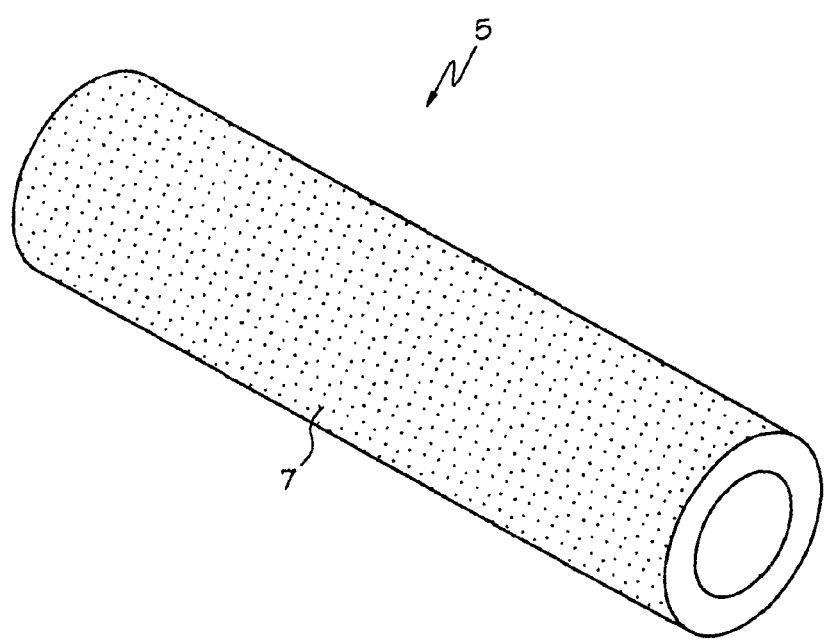
FIG. 1 is a side view of a catheter device comprising the fluorescent lubricant coating of the present invention on its surface.

While this invention may be embodied in many different forms, there are shown in the drawings and described in detail herein specific preferred embodiments of the invention. This description is an exemplification of the principles of the invention and is not intended to limit the invention to the particular embodiments illustrated.

In the broadest aspect, the lubricious coating composition of the present invention includes at least one hydrophobic lubricant, hydrophilic lubricant, or both, and a fluorescing agent. Alternatively, the lubricant itself may be fluorescenated, comprising fluorescent groups on the molecules. The fluorescent characteristic allows for easy inspection to determine the presence and location of a lubricious coating on a medical device.

Very little limitation is placed on the type of lubricant that may be utilized in the present invention. In fact, the fluorescent dyes may be utilized with any lubricant useful for medical device applications. The lubricants useful herein are either hydrophobic or hydrophilic in nature, and may be mixtures of both. Alternatively, the lubricant itself may be fluorescenated, comprising fluorescent groups on the molecules. In some preferred embodiments of the present invention, the lubricants are hydrophobic, particularly silicone based. Other hydrophobic lubricants include olive oil, cotton seed oil, linseed oil, sesame oil, glycerine, and so forth.

An even more specific example of a hydrophobic silicone lubricant is a blend of a hydrolyzable siloxane, such as an amino terminated siloxane. In one particular embodiment of the present invention, the amino terminated hydrolyzable siloxane is blended with a non-crosslinkable silicone oil. The crosslinkable siloxane is capable of crosslinking on a substrate surface and the non-curing silicone acts as a plasticizer for the crosslinked siloxane and may result in swelling of the crosslinked polymer. This combination results in a gel-like coating. In this particular example, the non-curing silicone provides lubricity. This type of system can offer advantages over a non-curing silicone lubricant in that the non-curing system has more opportunity to migrate.

A specific example of this type of system is a blend of Dow Corning DC-360 non-curing polydimethylsiloxane (PDMS) and SILASTIC® MDX4-4159 amino terminated polydimethyl siloxane also available from Dow Corning in Midland, Mich. and described in U.S. Pat. No. 4,904,433 and U.S. Pat No. 3,574,673 both of which are incorporated by reference herein in their entirety. Another useful siloxane of this type is SILASTIC® MDX4-4210. Sesame oil can replace the non-curing PDMS as the lubricant.

Other moisture curable silanes or siloxanes may be utilized in the present invention as well including those with various terminal groups that are activated by moisture. Examples of such systems are given in U.S. patent application Ser. No. 09/697,194 filed Oct. 26, 2000, the contents of which are incorporated by reference herein in their entirety.

While in some particular embodiments of the present invention, a hydrophobic lubricant is utilized, it will be appreciated that hydrophilic lubricants may be utilized as well, alone or in combination with the hydrophobic lubricants.

Hydrophilic lubricants useful herein include the category of lubricants known in the art as "hydrogels". These are polymeric materials which are hydrophilic in nature and have the ability to dissolve or swell in an aqueous environment. The polymeric materials are capable of manifesting lubricity while in a "wet" state, and when hydrated, exhibit low frictional forces in humoral fluids such as saliva, digestive fluids and blood, as well as saline solution and water. Hydrogels may be comprised of various materials including poly(ethylene oxides) optionally linked to a substrate surface by an interpenetrating network (IPN) with another polymer, polyalkylene glycols, alkoxy polyalkylene glycols, copolymers of methylvinyl ether and maleic acid, poly(N-acrylamides), poly(acrylic acids), poly(vinyl alcohols), poly(ethyleneimines), polyamides, methyl cellulose, carboxymethyl cellulose, polyvinyl sulfonic acid, heparin, dextran, modified dextran, chondroitin sulfate, and so forth.

Other crosslinkable hydrophilic lubricants include, but are not limited to esterified polymers, amides, anhydrides, halides, ethers, hydrolyzates, acetals, formals, alkylols, quaternary polymers, diazos, hydrazides, polyurethanes, sulfonates, nitrates and ion complexes.

Hydrogels are discussed in U.S. Pat. No. 6,120,904, U.S. Pat. No. 6,080,488, U.S. Pat. No. 6,040,058, U.S. Pat. No. 6,030,656, U.S. Pat. No. 6,017,577, U.S. Pat. No. 5,919,970, U.S. Pat. No. 5,662,960, U.S. Pat. No. 5,576,072, each of which is incorporated by reference herein in its entirety.

Other hydrophilic lubricants not specifically mentioned herein also find utility in the present invention. There is an endless variety of lubricious compounds that may be selected and one of skill in the art is aware of the vast number of which may be selected. The above exemplifications are therefore not intended to place any limitation on which lubricants are selected.

The fluorescing agents useful for admixing with the lubricants of the present invention exhibit an emission spectrum when exposed to radiation at a wavelength between about 200 nm and 1100, more suitably between about 200 nm and about 800 nm, and even more suitably between about 250 nm and about 450 nm. Those exhibiting spectra over about 500 nm may actually be classified in the visible region, and above this wavelength, may impart color to a substrate, a characteristic which may not be desirable for a medical device. Most typically, fluorescent dyes when, in solution, or when applied to a substrate, absorb ultraviolet (UV) light, (such as from daylight @ 300–430 nm) and re-emit most if the absorbed energy as blue fluorescent light between @ 400 and 500 nm.

Fluorescent dyes are typically colorless to weakly colored organic compounds that, in solution, or, when applied to a substrate impart little color to the substrate, a characteristic that is particularly desirable for most, but not all applications, in the medical device industry. Fluorescent dyes typically absorb light at one wavelength, and then re-emit the light at a slightly longer wavelength. Fluorescent dyes can, in fact, re-emit light by either fluorescence, or by phosphorescence after having absorbed light in the ultraviolet region, for instance. Phosphorescence differs from fluorescence in the amount of time that the compound luminesces. Phosphorescence can typically be visually observed for a considerable period of time of up to hours, whereas fluorescence is visually observed for a shorter, more immediate period of time.

Some common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; rare earth chelates; carbazoles; derivatives thereof; and the like.

Rhodamine dyes and fluorescein dyes may be utilized in some embodiments of the present invention. Rhodamine dyes are a subclass of xanthene dyes in which the xanthene ring is a rhodamine-type parent xanthene ring. Typical rhodamine dyes include, but are not limited to, rhodamine B; 5-carboxyrhodamine; rhodamine X; 4,7-dichlororhodamine X; rhodamine 6G; rhodamine 110; 4,7-dichlororhodamine 110; tetramethyl rhodamine; and 4,7-dichlorotetramethylrhodamine. Other typical rhodamine dyes can be found, for example, in U.S. Pat. No. 6,080,852, U.S. Pat. No. 6,025,505, U.S. Pat. No. 5,936,087, U.S. Pat. No. 5,750,409, U.S. Pat. No. 5,366,860, U.S. Pat. No. 5,231,191, U.S. Pat. No. 5,840,999, U.S. Pat. No. 5,847,162, WO 99/36960; Sauer et al., 1995, J. Fluorescence 5(3): 247–261; Arden-Jacob, 1993, Neue Lanwellige Xanthen-Farbstoffe fur Fluoreszenzsonden und Farbstoff Laser, Verlag Shaker, Germany; and Lee et al., 1992, Nucl. Acids Res. 20(10):2471–2483, all of which are incorporated by reference herein in their entirety.

Fluorescein dyes refer to the subclass of xanthene dyes in which the parent xanthene ring is a fluorescein-type parent xanthene ring. Typical fluorescein dyes include, but are not limited to, 5-carboxyfluorescein and 6-carboxyfluorescein. Additional typical fluorescein dyes can be found, for example, in U.S. Pat. No. 6,008,379, U.S. Pat. No. 5,750, 409, U.S. Pat. No. 5,066,580, U.S. Pat. No. 4,439,356, U.S. Pat. No. 4,481,136, U.S. Pat. No. 5,188,934, U.S. Pat. No. 5,654,442, and WO 99/16832, all of which are incorporated by reference herein in their entirety.

Other general classes of useful fluorescent dyes include, but are not limited to acrylamides; phenyls and biphenyls; 4,4'-distyrylbiphenyls; phenylenes; benzenes and distyrylbenzenes; fused aromatic compounds such as naphthalenes, anthracenes, phenanthrenes, chrisenes, pyrenes, triphenylenes, pentacenes, pentha pentaphenes, perylenes, hexaphenes, coronenes, rubrenes, dibenzocoronenes, fluoranthenes, and so forth; pyrenes with aminocoumarin conjugates; flourescein isothiocyanate polymer conjugates; fluorescein salts such as lithium fluoresceinate; eosines and erythrosins (xanthenes); benzothioxanthenes; benzoxanthenes; hydroxy erythrosins; benzoxazoles, stilbenzylbenzoxazoles, bis(benzoxazoles), nitrobenzoxadiazoles and hydroxy nitrobenzoxadiazoles; furans ans benzo[b] furans and bis(benzo[b] furan-2-yl) biphenyls; benzimidazoles and cationic benzimidazoles; benzimidstilbenes, hydroxystilbenes, divinylstilbenes and triazinyl amino stilbenes; nitrobenzoxadiazoles; naphthalimides; quinolines; acridines, acidoacridines, hydroxyacridines, and acridones; acidoacridines; carbazoles; hydroxy cyanines, carbocyanines (phenylcarbocyanines and hydroxycarbocyanines), and merocyanines; pyridinium salts and hydroxy-substituted pyridinium salts; oxonols; resorofins and hydroxy resorofins; xanthiones; pyridines; pyrazolines; dihydropyrimidines; thiazoles; stilbenzyl-2H-triazoles; flavones; and so forth; and fluorescent derivatives thereof.

Some of the above compounds or their derivatives will produce phosphorescence in addition to fluorescence, or will phosphoresce only. Some phosphorescent compounds include porphyrins, phthalocyanines, polyaromatic compounds such as pyrenes, anthracenes and acenaphthenes, and so forth.

More specific examples of fluorescent dyes suitable for use herein include, but are not limited to, fluorescein-5-isothiocyanate, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine (and other rhodol derivatives described in U.S. Ser. No. 07/509,360 (filed Apr. 16, 1990) incorporated by reference), rhodamine 101 sulfonyl chloride sold under the tradename of TEXAS REDS®, 5-iodoacetamido fluorescein; 6-iodoacetamido fluorescein; 5-carboxy-2',7'-dichlorofluorescein; 5-aminofluorescein; 5-carboxyseminaphthofluorescein, 5-carboxynaphthofluorescein; 5-bromomethylfluorescein; fluorescein-5-maleimide; N-methylacridine; N-phenylacridine; 5-(dichlorotriazinyl)aminofluorescein; 9-methyl acridine; eosin-5-iodoacetamide; Lissamine rhodamine B sulfonyl cadaverine, 1,2-di(5-methylbenzoxazol-2-yl)ethylene, 5-hydroxycoumarin, 4-methyl-7-hydroxycoumarin, 7-dialkylamino-4-methylcoumarin; 4-bromomethyl-7-methoxycoumarin; 4-bromomethyl-7-hydroxy coumarin; 5-iodoacetamide; N-(1-pyrene) iodoacetamide; 1-pyrenemethyl iodoacetate; pyrenyloxy sulfonic acids; dialkylaminocoumarin pyrenes; 6,6'-dibromostilbene; 9-methylacidoacridine; hydroxy-9-methylacidoacridine; N-methylcarbazole; hydroxy-n-methylcarbazole; 4-chloro-7-nitrobenz-2-oxa-1,3-diazole; 6-hydroxyquinoline; 6-aminoquinoline; 1,6-diphenyl-1,3,5-hexatriene; 1-(4-dimethyl aminophenyl)-6-phenylhexatriene and corresponding 1,3-butadienes; 2-(7-nitrobenz-2-oxa-1, 3-diazole-4-yl)methylaminoacetalkdehyde; 6-(7'-nitrobenz-2-oxa-1,3-diazole-4-yl)aminohexanoic acid; erthyrosin-5-maleimide; N-methyl-4-acetylamino-1,8-naphthalimide; 2,3,5-triphenylpyrazoline; 2,4,6-trimethyl-3,5-di (ethoxycarbonyl)-1,4-dihydropyrimidine; 1-phenyl-2-(benzothiazol-2-yl) ethylene, acridine yellow, acridine orange, uranine,d phloxine, Rose Bengale, Rhodamine B, Rhodamine 6G, rosamine, tripaflavine, benzoflavin, thionine, safranine, phenosafranine, magdarared, resrufine and methylene blue, quinolines such as 8-aminoquinaldine, 4-(4-ethoxyphenyl) thiazole; 4,5-diaminopyridine; 4(4-dialkyldiaminostyryl)-N-methyl pyridinium iodate; 2,5-diphenyloxazole; 5,6-dimethoxy-3-hydroxyflavone; 3-amino-acridine; stilbenzyl-2H-naphthol[1,2-d] triazole; 3,3'-bis-(3-sulfopropyl-5,5'-dichloro-9-cetylthiacarbocyanine; CASCADE BLUE®, a pyrenyloxy sulfonic acid available from Molecular Probes, Inc., BLANKOPHOR® CA 4410 available from Bayer Corp. in Pittsburgh, Pa. (parent company is Bayer AG in Germany); Fibers, Additives and Rubber Division; such as ALEXA FLUOR® 350 (carboxylic acid succinimidyl ester), AMCA-X Dyes (succinimidyl ester); succinimidyl ester mixed isomers (i.e. of sulforhodamine 101) such as RHODAMINE RED® (or TEXAS RED-X®) available from Molecular Probes, Inc., Fluorescent dyes are available from, for example, Molecular Probes, Inc. (MPI) in Eugene, Oreg. Benzoxazoles and derivatives thereof are available from Ciba Geigy in Tarrytown, N.Y. under the tradename of UVITEX® such as UVITEX® OB, 2,5-bis(5-tert-benzoxazoly-2-) thiophene which is an odorless primrose yellow crystal powder. UVITEX® OB is a more hydrophobic compound being quite soluble in chlorobenzene.

Fluorescent dyes are discussed in U.S. Pat. No. 4,452,720, U.S. Pat. No. 5,227,487, U.S. Pat. No. 5,543,295 and in Ullman's Encyclopedia of Industrial Chemistry Vol. A18 (5th Edition) pp. 153–167 all of which are incorporated by reference herein in their entirety. As noted above, particularly preferred dyes are biocompatible and hydrophilic in nature.

In some embodiments of the present invention, xanthene dyes are utilized including the rhodamine dyes and the fluorescein dyes.

In some embodiments of the present invention, the dyes are suitably hydrophilic, and more suitably are biocompatible. They may, however, exhibit only one quality or the other, or both. Specific hydrophillic fluorescent dyes suitable for use herein include 5-carboxyfluorescein (emits at a wavelength of about 494 and emits at about 518 nm); 6-carboxyfluorescein (495/521 nm); fluorexon dyes; indocyanine green; Rose bengal (fluorescein derivative or xanthene dye); lissamine green triarylmethane dye; the 4,7-dichlorofluoresceins such as 4,7-chloro-5- (and 6-) carboxyfluorescein dyes and 1',2',7',8'-dibenzo-4,7-dichlorofluoresceins described in U.S. Pat. No. 5,188,934 incorporated by reference herein; or some mixture thereof. Such dyes are currently used in hospitals and clinics as diagnostic agents for many human diseases. Some water-soluble xanthene type dyes are described in U.S. Pat. No. 6,191,278 incorporated by reference herein in its entirety.

The above lists are by no means exhaustive. The compounds available for use herein are too numerous to mention. The above are therefore intended for exemplary purposes only and should in no way be intended to limit the scope of the present invention.

The lubricant and fluorescing agent are desirably admixed. This may be accomplished in a solvent or cosolvent blend. The selection of solvent(s) will depend on the choice of lubricant, as well as the choice of fluorescing agent. Hereinafter, the term mixture will be used to include a solution, dispersion, emulsion or suspension.

Useful polar solvents include, but are not limited to, water, $C_3$–$C_8$ alcohols such as ethanol, isopropanol and methanol, stearyl alcohol, ethylene glycol, propylene glycol, glycerin, and so forth.

Useful nonpolar solvents include, but are not limited to, aliphatic hydrocarbons including heptane and hexane; aromatic hydrocarbons such as toluene and xylene; chlorinated hydrocarbons such as perchloroethylene, methylene chloride, chloroform, carbon tetrachloride, 1,1,1-trichloroethane; fluorocarbons; mineral spirits; and so forth.

A cosolvent blend may be utilized, particularly when the lubricant is hydrophobic and the fluorescing agent is hydrophilic. For instance, a blend of isopropanol and hexane are useful in this case.

In a particular embodiment of the present invention, the silicone based lubricant is polydimethylsiloxane. Due to the extreme hydrophobicity of polydimethylsiloxane, it is difficult to dissolve the dye directly in the lubricant. At best, most dyes will only be suspended, and not fully solubilized in the lubricant. Consequently, it is desirable in this instance to utilize a solvent, and more preferably, a cosolvent blend to admix the dye and the lubricant. The cosolvent blend includes a polar solvent for admixture of the hydrophilic dye, and a nonpolar solvent for admixture of the hydrophobic lubricant. This cosolvent blend will also help facilitate solution stability when the two compounds have quite different solubilities. While a cosolvent system is desirable if the lubricant is hydrophobic and the dye is hydrophilic, it may not be preferable if both the lubricant and the dye are hydrophobic, or if both are hydrophilic. In this embodiment, an aliphatic hydrocarbon solvent such as heptane can be used to solvate the polydimethylsiloxane and isopropanol can be used to solvate the hydrophilic fluorescing agent such as 5-carboxyfluorescein.

Optionally, a surfactant may be advantageously utilized in the present invention in stead of, or in addition to using a cosolvent blend. A surfactant is capable of reducing the interfacial tension between distinct phases, i.e. a hydrophobic and a hydrophilic phase because a surfactant has a hydrophobic and a hydrophilic portion on the same molecule. If a surfactant is utilized, a cosolvent blend may no longer be necessary when using a hydrophobic lubricant with a hydrophilic fluorescent dye, or the opposite. While the surfactant is optional, it is preferable for use in the present invention to assure a uniform solution. The hydrophilic nature of the dye and the extreme hydrophobicity of the lubricant make them incompatible for mixing. Furthermore, it is desirable that the surfactant be biocompatible. A surfactant will facilitate mixing and preparation of a solution of the hydrophilic dye and the hydrophobic lubricant. Furthermore, the surfactant will also improve solution stability over time and aid in preventing separation of the solution and settling. Settling or separation could result nonuniformity in the coating, ultimately resulting in parts of an article that have no coating at all while other parts of the same coated article could be more heavily coated than is desirable.

The surfactants useful herein include nonionic, anionic, cationic or amphoteric surfactants. Nonnionic surfactants are preferably utilized in some embodiments herein. Examples of nonionic surfactants include, but are not limited to, poly-(oxyethylene) poly-(oxypropylene) block copolymers (EO/PO block copolymers) available from BASF under the tradename of PLURONIC® such as PLURONIC® F68 or PLURONIC® L-44 and those available from Uniqema under the tradename of POLOXAMER® such as POLOXAMER® 124, polyoxyethylene sorbitan esters available from Uniqema under the under the tradename of TWEEN® such as polyoxyethylene sorbitan monolaurate, polyoxyethylene sorbitan monopalmitate, polyoxyethylene sorbitan monostearate, and polyoxyethylene sorbitan monooleates, and sorbitan esters available from under the tradename of SPAN® such as sorbitan monolaurate, sorbitan monostearate, and sorbitan monooleate, and ethoxylates such as octyl phenol ethoxylates available from Mallinckrodt Chemicals in Phillipsburg, N.J. under the tradename of TRITON® and nonyl phenol ethoxylates, and so forth.

Other examples of specific surfactants useful herein include, but are not limited to, PEG-400 (polyethylene glycol), dimyristyl phosphatidyl glycerin (DMPG), the salt of a bile acid such as cholic acid, deoxycholic acid, or taurocholic acid, ammonium salts of allyl phosphate made by Vanderbilt company under the tradename of DARVAN® L.

The surfactant may also itself act as a lubricant. Some examples of surfactants having lubricating properties as well include silicone based surfactants such as block copolymer polyalkylene oxide-modified polydimethylsiloxanes, amino-modified silicone polyether copolymers, alkylene oxide modified silicone glycols, and so forth. This type of surfactant is available from OSI Specialties, Inc. under the tradename of SILWET® which are polyalkylene oxide-modified polydimethylsiloxane block copolymers. Such surfactants/lubricants can also be used in combination with other lubricants in the present invention. Such surfactants/lubricants are discussed in U.S. Pat. No. 6,046,143 incorporated by reference herein in its entirety.

The lubricious coating may be applied to any surface of a medical device using any method known in the art including dipping, spraying, painting, and so forth.

Useful energy sources for detection of the fluorescent composition include ultraviolet radiation, electron beam radiation, and so forth.

The method of the present invention, in its broadest aspect, allows for the detecting of a lubricious coating on the surface of an article, particularly medical devices. The method includes the steps of admixing a fluorescent compound and a lubricant, or alternatively providing a fluorescenated lubricant wherein the lubricant itself has fluorescent groups, coating the surface of the device with the admixture, irradiating the surface of the device with a source of energy capable of inducing fluorescent emission, and observing the coating for its presence and location.

Examples of medical devices according to the invention include intraluminal medical devices such as catheters including balloon catheters and stent delivery catheters, vena-cava filters, stents, stent-grafts, and so forth.

In one embodiment of the present invention, the composition and method are utilized in combination with a stent delivery device. More specifically, the lubricious coating is provided on the surface of at least one stent retaining sleeve. The method of the present invention can then be utilized to detect the presence and location of the lubricious coating on the stent retaining sleeve(s). It is very important to the deployment of a stent that the stent retaining sleeves be adequately lubricated.

In some stent delivery devices, the stent is held in place around the catheter prior to and during percutaneous delivery by means of one, and preferably two, end sleeves in order to maintain their reduced diameter configuration during delivery of the stent to its deployment site. Typically the stent is of the balloon inflatable type, but it can be a self expanding stent as well. Lubricious coatings are typically utilized on such devices not only to facilitate insertion of the catheter into the patient's vasculature, but also to increase the ease with which the stent may be deployed. In the latter case, the lubricious coating is found on the under surface of the stent retaining sleeve. It is difficult in the latter case to observe not only whether or not the coating has been laid down, but it is also extremely difficult to ascertain the uniformity of the coating.

The present invention is further exemplified in the following FIGS. 1–5 which will hereinafter be discussed. FIG. 1 shows generally at 5, a simplified tubular structure useful in intraluminal medical devices. The tubular structure shows on its surface, the fluorescent dyed lubricious coating 7, of the present invention. In this embodiment, the coating can include a hydrophobic lubricant and a biocompatible, hydrophilic fluorescent dye.

Figure 2:
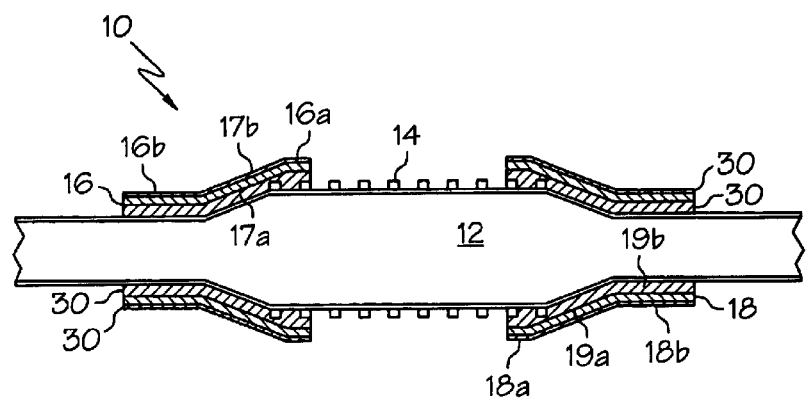
FIG. 2 is a side view of a stent delivery system illustrating the fluorescent lubricant coating of the present invention on both the inner surface and outer surface of the stent retaining sleeves.

FIG. 2 shows an embodiment of the present invention wherein a catheter generally designated 10 has an expandable portion or balloon 12. The expandable portion may be an inherent part of the catheter, as shown, or alternatively may be a separate balloon which is affixed to the catheter in any of the manners which may be known to one of ordinary skill in the art. Disposed about balloon 12 is a stent 14 as shown. Stent 14 may be any stent type capable of being delivered by a stent delivery catheter, such stents may be self-expanding of balloon expandable.

Attached to the catheter 10 are a pair of stent retaining sleeves 16, 18. When the balloon 12 in the non-inflated state first sleeve portions 16a, 18a overlay the ends of balloon 12 as well as the ends of stent 14 as shown. Sleeves 16 and 18 also include respective second portions 16b and 18b. Regardless of the state of the balloon 12, non-inflated or inflated, second sleeve portions 16b, 18b are fixedly attached to catheter 10. The second sleeve portions may be attached to the catheter utilizing any method of attachment known.

Figure 3:
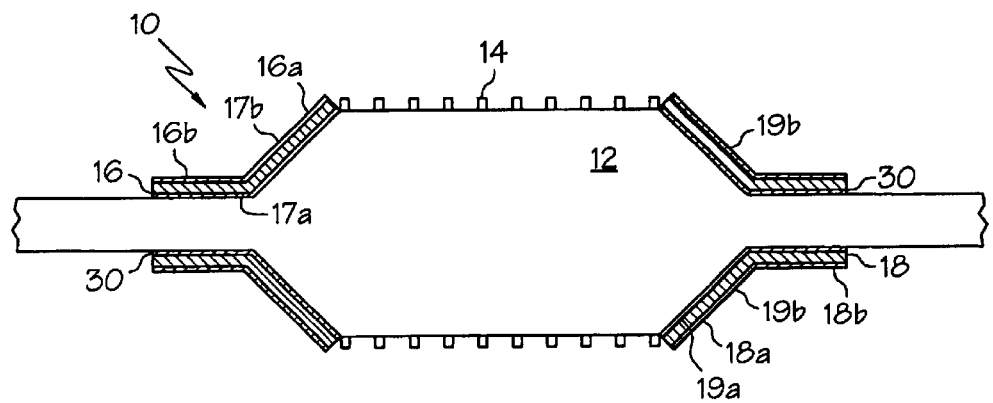
FIG. 3 is a side view of a the same stent delivery system as shown in FIG. 2 but with the stent in its expanded state.

In the embodiment shown in FIG. 2, the fluorescenated lubricious coating 30 is disposed on both the inner surface 17a, 19a and outer surface 17b, 19b of sleeves 16, 18. However, the fluorescenated lubricious coating may be disposed about either the inner surface 17a, 19a or outer surface 17b, 19b of sleeves 16, 18. FIG. 3 is representative of the same device shown in FIG. 2 but shows the balloon in its expanded state and the stent consequently in its deployed state.

Figure 5:
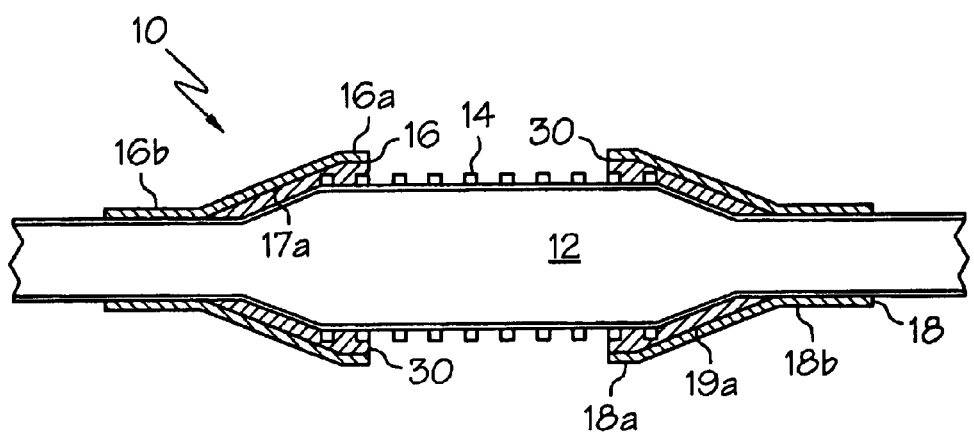
FIG. 5 is a side view of a stent delivery system illustrating the fluorescent coating of the present invention on a portion of the inner surface of the stent retaining sleeves.

A lubricious coating on the outer surfaces provides improved trackability and maneuverability of the catheter through the body lumen, while a lubricious coating on the inner surface facilitates proper and smooth deployment of the stent by facilitating retraction of the sleeves thereby assisting deployment of the stent. The lubricious coating assists stent 14 deployment by allowing the ends of the balloon 12 and stent 14 to slide more readily away from the sleeves when balloon 12 is inflated, as shown in FIGS. 3 and 5. Once the ends of stent 14 are no longer overlaid by sleeves 16 and 18, the stent is allowed to fully expand as shown in FIG. 3.

Figure 4:
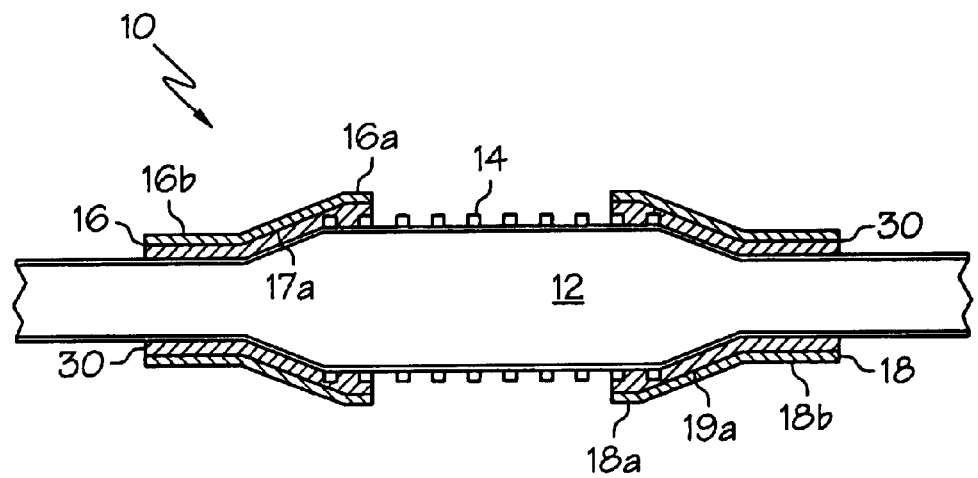
FIG. 4 is a side view of a stent delivery system illustrating the fluorescent coating of the present invention on the inner surface of the stent retaining sleeves.

While FIGS. 2 and 3 illustrate an embodiment in which both the inner and outer surfaces 17a, 19a and 17b, 19b consecutively, of stent retaining sleeves 16, 18 are coated, FIGS. 4 and 5 illustrate an embodiment in which just the inner surfaces 17a, 19a of stent retaining sleeves 16, 18 are coated.

FIG. 5 illustrates an embodiment in which only a portion of the inner surface 17a, 19a of the stent retaining sleeves 16, 18 are coated with the fluorescenated lubricious coating of the present invention.

Figure 6:
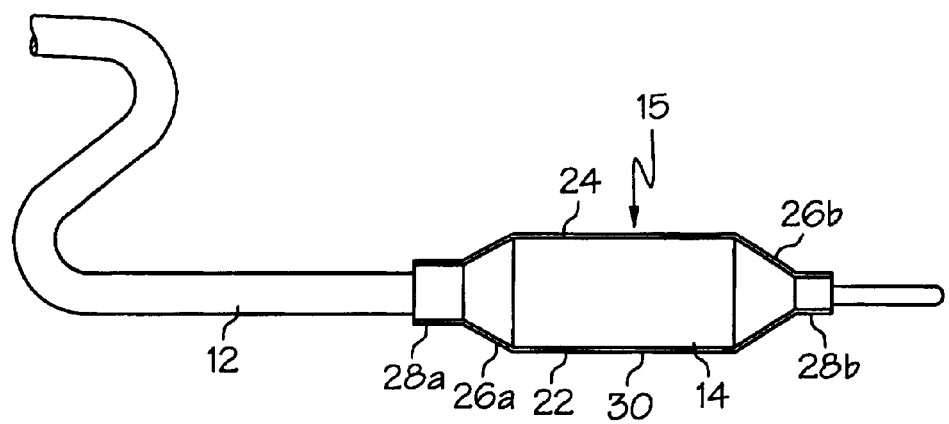
FIG. 6 is a side view of an inflated dilatation balloon catheter wherein the fluorescent coating of the present invention is on the outer surface of a dilataton balloon.

FIG. 6 illustrates generally at 15 a dilatation balloon catheter wherein the dilatation balloon or inflatable portion 14 is shown in its expanded state. Balloon 14 has a body 24, cones 26a, 26b and waist portions 28a, 28b. The fluorescent lubricious coating 20 of the present invention is shown on the outer surface 22 of the dilatation balloon. In this instance, the coating 30 is found on the body 24, cone portions 26a, 26b and waist portions 28a, 28b. Optionally, the coating 30 may be provided on only the body 24, or on any combination of the body 24, cones 26a, 26b and waist portions 28a, 28b, and does not have to be provided on all.

Figure 7:
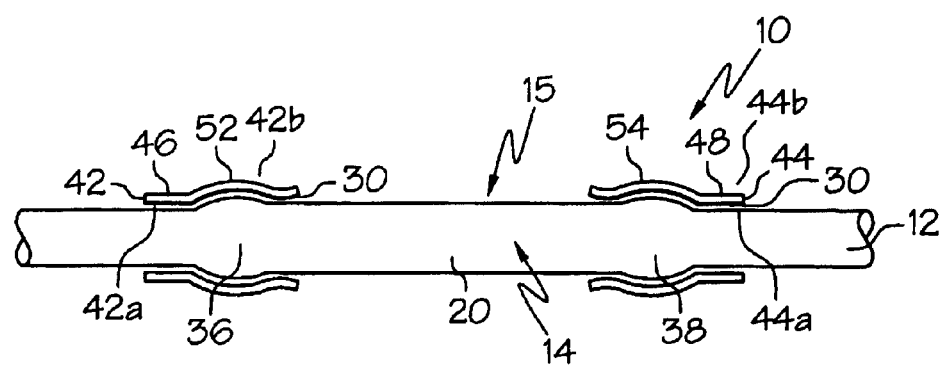
FIG. 7 is a side view of a dilatation balloon having retaining sleeves for maintaining a balloon in a crimped state.

FIG. 7 illustrates generally at 15 a dilatation balloon catheter wherein the dilatation balloon or inflatable portion 14 is shown in a crimped state. Balloon 14 has a elongated body portion 20, a proximal end 36 and a distal end 38. Balloon 14 is crimped with retaining sleeves 42, 44 which have catheter attachment portions 46, 48 and margin retaining portions 52, 54. The retaining sleeves 42, 44 have a fluorescent lubricious coating 30 on the inner surface of the sleeves 42a, 44a. Optionally, the retaining sleeves may be over the proximal end 36, the distal end 38, or both.

In these particular embodiments described above, the fluorescenated lubricious coatings are utilized on the inner surfaces 17a, 19a of the stent retaining sleeves 16, 18. as shown in FIGS. 2–5. It is particularly advantageous to utilize the fluorescenated coatings of the present invention on the inner surface 17a, 19a of the sleeves 16, 18, because in this location it is particularly difficult to ascertain whether the lubricious coating has been properly applied, or if it is present at all.

Variations on the coating of stent retaining sleeves with lubricious coatings is discussed in copending U.S. application Ser. No. 09/697,194 incorporated by reference herein in its entirety.

In the present invention, the lubricious coatings have been fluorescenated through the addition of a fluorescent dye so that upon exposure of the device to a source of energy capable of inducing a fluorescent emission, the fluorescing agent will exhibit a known emission spectrum thus allowing observation of the coating presence, location or uniformity. This permits determination of the continuity and consistency of the coverage of the coating on the surface of the device.

For this purpose, any fluorescent dye may be added to the lubricious coatings of the present invention.

The electromagnetic radiation used to irradiate the surface of the device is preferably in the ultraviolet spectrum and preferably has a wavelength between about 250 and 500 nm, and more preferably about 300 to 450 nm. Any suitable energy source with these known characteristics will work including ultraviolet, fluorescent light and electron beam radiation.

The detector device may be any type of photometer including an ultraviolet (UV) digital camera. Detection may be by way of ultraviolet light detection, fluorescent light dectection, photo camera, electron beam detection, for instance, and so forth. If a digital camera is selected, it is then preferably compatibly linked to a computer having appropriate software. The computer may also be internally networked for image capturing and storage.

The method of the present invention allows for a quick and accurate detection method while operating at normal production speeds. Furthermore, it offers some assurance that adequate amounts of lubricious coatings are being provided on the surface of the medical device without having to apply an excess amount of coating.

The following nonlimiting examples further illustrate the present invention but are in no way intended to limit the scope thereof.

EXAMPLES

Dye 1

A fluorescent dye, 5-carboxyfluorescein (Sigma Chemical, Aldrich Chemical, >95% active, red), 1.0 g, was dissolved in 25 ml isopropanol (Aldrich Chemical, 99.9%, PRA grade) along with 5.0 g of PLURONIC® L-44 EO/PO block copolymer surfactant, and 1.25 g glycerol (Sigma Chemical, >99%, liquid, chemical grade). The resultant blend was 4 wt-% dye, 20 wt-% surfactant and 5 wt-% glycerol.

The mixture was stirred mechanically for more than 2 hours to ensure that all of the dye has been dissolved. The resultant mixture is a clear, dark yellow color.

Dye 2

The same procedure was followed as in example 1 except the dye was added at 0.2 g (<1 wt-%), the surfactant at 1.0 g (20 wt-%) and the glycerol at 0.8 g (5 wt-%) to 10 ml of isopropanol.

As before, the mixture was stirred for more than 2 hours.

Slipcoat 1

A 6% silicone lubricant mixture was prepared by mixing 4% polydimethylsiloxane (Dow Corning DC-360) and 2% of an amino terminated polydimethylsiloxane (MDX4-4159 also available from Dow Corning) in a heptane solvent.

Example 1

Dye mixture 1 (2.5 ml) was added to a slipcoat mixture 1 (47.5 ml). The two mixtures were then further mixed together by shaking and a yellowish, cloudy solution is formed. The resultant dye concentration was <0.2 wt-%, PLURONIC® L-44 was about 1.0 wt-% and the glycerol is about 0.25 wt-%. The mixture was stored in a freezer at <4° C. and kept free of moisture.

The resultant dye/slipcoat mixture was then tested on a stent delivery device by injecting the dye/slipcoat mixture on the inner surface of a stent retaining sleeve. The mixture was injected only once using about 1 ml of mixture. The coating was excited using an ultraviolet lamp manufactured by UVP in California at a wavelength of 365 nm.

Fluorescence was detected using a Micro-Mac AF-01 autofocus digital camera manufactured by Techniquip in California and equipped with imaging software in a PC computer. The camera was provided in a black box which was also equipped with two UV lamps.

In contrast, a slipcoat mixture, without fluorescent dye, is injected twice in order to ensure an adequate lubricious coating.

Example 2

The same procedure was followed as in Example 1 to make a fluorescent dye/lubricant mixture. The resultant dye concentration was <0.2 wt-%, PLURONIC® L-44 was at a concentration of 1.0 wt-% and the glycerol at about 0.25 wt-%. Again, the dye was injected on the inner surface of a stent retaining sleeve. The same procedure was followed as in Example 1.

What is claimed is:

1. A method for detecting the presence and uniformity of a lubricious coating on a medical device comprising the steps of:
   a) preparing a mixture of at least one fluorescing agent which is a xanthene, a triarylmethane or mixture thereof and at least one lubricant;
   b) applying said mixture to the surface of a medical device to form a coating capable of exhibiting fluorescence; and
   c) subjecting the surface of the medical device to a source of energy capable of inducing a fluorescent emission; and
   d) observing the fluorescent emission to determine the location, uniformity or both of said lubricant.

2. The method of claim 1 wherein said fluorescing agent is a fluorescein, a rhodamine, a derivative thereof, or mixture thereof.

3. The method of claim 1 wherein said hydrophobic lubricant is a silicone based lubricant.

4. The method of claim 1 wherein said hydrophobic lubricant is a polydimethylsiloxane.

5. The method of claim 4 wherein said polydimethylsiloxane is utilized in combination with a crosslinkable silicone.

6. The method of claim 1 wherein said mixture further comprises a surfactant.

7. The method of claim 6 wherein said surfactant is biocompatible.

8. The method of claim 6 wherein said surfactant is nonionic.

9. The method of claim 8 wherein said surfactant is an ethylene oxide/propylene oxide block copolymer.

10. The method of claim 1 wherein said fluorescing agent is hydrophilic.

11. The method of claim 10 wherein said fluorescing agent is a hydrophilic fluorescing agent is a 5-carboxyfluorescein, 6-carboxyfluorescein, fluorexon, lissamine green, indocyanine green, rose bengal or mixture thereof.

12. A method for detecting the presence and uniformity of a lubricious coating on a medical device comprising the steps of:
   a) preparing a mixture of at least one fluorescing agent and mixtures thereof and at least one lubricant using a cosolvent blend;
   b) applying said mixture to the surface of a medical device to form a coating capable of exhibiting fluorescence; and
   c) subjecting the surface of the medical device to a source of energy capable of inducing a fluorescent emission; and
   d) observing the fluorescent emission to determine the location, uniformity or both of said lubricant.

13. The method of claim 12 wherein said cosolvent blend comprises at least one alcohol and at least one straight chain hydrocarbon.

14. The method of claim 13 wherein said at least one alcohol is isopropanol and said at least one hydrocarbon is heptane, hexane or a mixture thereof.

15. A method for detecting the presence and uniformity of a lubricious coating on a medical device comprising the steps of:
   a) preparing a mixture of at least one hydrophilic fluorescing agent and mixtures thereof and at least one lubricant;
   b) applying said mixture to the surface of a medical device to form a coating capable of exhibiting fluorescence; and
   c) subjecting the surface of the medical device to a source of energy capable of inducing a fluorescent emission; and
   d) observing the fluorescent emission to determine the location, uniformity or both of said lubricant.

* * * * *